United States Patent
Haga et al.

(10) Patent No.: US 9,487,522 B2
(45) Date of Patent: Nov. 8, 2016

(54) SSH-2 (SLINGSHOT-2) INHIBITORS AND METHODS FOR MAKING AND USING THEM

(75) Inventors: Jason H. Haga, San Diego, CA (US); Shu Chien, La Jolla, CA (US); Matt Mui, La Jolla, CA (US); Marshall J. Levesque, Philadelphia, PA (US); Phillip D. Pham, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 50 days.

(21) Appl. No.: 14/005,653

(22) PCT Filed: Mar. 15, 2012

(86) PCT No.: PCT/US2012/029267
§ 371 (c)(1),
(2), (4) Date: Nov. 25, 2013

(87) PCT Pub. No.: WO2012/129057
PCT Pub. Date: Sep. 27, 2012

(65) Prior Publication Data
US 2014/0094466 A1     Apr. 3, 2014

Related U.S. Application Data

(60) Provisional application No. 61/454,148, filed on Mar. 18, 2011.

(51) Int. Cl.
*C07D 487/04*     (2006.01)
*C07D 237/32*     (2006.01)
*C07C 311/17*     (2006.01)
(Continued)

(52) U.S. Cl.
CPC .......... *C07D 487/04* (2013.01); *A61K 31/192* (2013.01); *A61K 31/365* (2013.01); *A61K 31/4025* (2013.01); *A61K 31/422* (2013.01); *A61K 31/451* (2013.01); *A61K 31/497* (2013.01); *A61K 31/502* (2013.01); *A61K 31/506* (2013.01); *A61K 31/519* (2013.01); *C07C 311/17* (2013.01); *C07D 211/96* (2013.01); *C07D 237/32* (2013.01);
(Continued)

(58) Field of Classification Search
None
See application file for complete search history.

(56) References Cited

PUBLICATIONS

Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*

(Continued)

*Primary Examiner* — San-Ming Hui
*Assistant Examiner* — Andrew Lee
(74) *Attorney, Agent, or Firm* — Greer, Burns & Crain, Ltd.; Gregory P. Einhorn

(57) ABSTRACT

In alternative embodiments, the invention provides compositions that inhibit the polypeptide SSH-2, or SlingSHot-2, a phosphatase enzyme that regulates actin filaments, and methods for making and using them, including methods comprising administering compositions of the invention to regulate or modify actin filament polymerization by inhibiting SSH-2, where in one embodiment compositions of the invention slow or inhibit F-actin depolymerization and severing. In alternative embodiments, compositions and methods of the invention are used to slow or inhibit cell motility and/or internal remodeling. In alternative embodiments, compositions and methods of the invention are used to slow or inhibit, or reverse, or ameliorate the progression of a cancer or a metastasis or other uncontrolled or unregulated cell growth, and/or Alzheimer's disease.

21 Claims, 10 Drawing Sheets

(51) Int. Cl.
*A61K 31/502* (2006.01)
*A61K 31/519* (2006.01)
*A61K 31/192* (2006.01)
*A61K 31/365* (2006.01)
*A61K 31/4025* (2006.01)
*A61K 31/422* (2006.01)
*A61K 31/451* (2006.01)
*A61K 31/497* (2006.01)
*A61K 31/506* (2006.01)
*C07D 211/96* (2006.01)
*C07D 307/90* (2006.01)
*C07D 417/06* (2006.01)
*A61K 9/127* (2006.01)

(52) U.S. Cl.
CPC ........... *C07D307/90* (2013.01); *C07D 417/06* (2013.01); *A61K 9/1271* (2013.01)

(56) References Cited

PUBLICATIONS

Baharlou, Simin, International Preliminary Report on Patentability issued in PCT/US2012/029267, The International Bureau of WIPO, Date of Mailing: Oct. 3, 2013.

Fenteany, G et al., "Small-molecule inhibitors of actin dynamics and cell motility", Current Topics in Medicinal Chemistry, 2003, 3(6):593-616.

Huang, et al. "Cofilin phosphatases and regulation of actin dynamics," Curr Opin Cell Biol 18: 26-31, 2006.

Lee, Dong Wook, International Search Report and Written Opinion issued in PCT/US2012/029267, Korean Intellectual Property Office, Date of Mailing: Sep. 14, 2012.

PubChem Compound, datasheet (online compound summary) Retrieved from the Internet: "URL: http://pubchem.ncbi.nlm.nih.gov/search/search.cgi", CID 4763376 (create date: Sep. 17, 2005).

PubChem Compound, datasheet (online compound summary) Retrieved from the Internet: "URL: http://pubchem.ncbi.nlm.nih.gov/search/search.cgi", CID 3776753 (create date: Sep. 11, 2005).

PubChem Compound, datasheet (online compound summary) Retrieved from the Internet: "URL: http://pubchem.ncbi.nlm.nih.gov/search/search.cgi", CID 2119389 (create date: Jul. 15, 2005).

Rao et al., "Microfilament Acting Remodeling as a Potential Target for Cancer Drug Development", Current Cancer Drug Targets, 2004, 4, 345-354.

Saito, "Toxins Affecting Actin Filaments and Microtubules", Prog Mol Subcell Biol. 2009;46:187-219.

Wang et al., "The cofilin pathway in breast cancer invasion and metastasis," Nat Rev Cancer. Jun. 2007;7(6):429-40.

* cited by examiner

ZINC05373221

ZINC06601214

ZINC 03377116

ZINC00260730

ZINC04307500

ZINC00053046

ZINC03313382

ZINC06737368

ZINC03271868

ZINC04110856

ZINC03429974

Figure 4A

Table 3. consensus ranking for new high potential inhibitors for SSH-2

| ZINC ID | SSH-2 | VHR | VH3 | PTEN | KAP | rVH6 (Pyst1) | mkp5 | mkp4 | VHY | MTMR2 | VH1 | DUSP18 | CDC25a |
|---|---|---|---|---|---|---|---|---|---|---|---|---|---|
| ZINC05373221 | 20 | 19691 | 5958 | 1630 | 19653 | 17795 | 15810 | 5769 | 14332 | 13291 | | 767 | 8752 |
| ZINC06601214 | 56 | 5615 | 11708 | 3432 | 20578 | 13533 | 20183 | 7226 | 1491 | 7223 | 1873 | | 18943 |
| ZINC03377116 | 138 | 659 | 19544 | 3112 | 15853 | 13994 | 9562 | 6250 | 14086 | 6903 | | | 10104 |
| ZINC00260730 | 175 | 7130 | 4148 | 7688 | 7086 | | 11210 | 5869 | 1041 | 5003 | 2083 | 3017 | 16958 |
| ZINC04307500 | 179 | 17657 | 129 | 5228 | 19920 | 8768 | 14312 | 6660 | 16807 | 5233 | 5237 | 1052 | 15747 |
| ZINC00053046 | 54 | 2072 | 6091 | 5934 | 3904 | 14334 | 19755 | 16725 | 16892 | 3327 | 359 | 1092 | 12249 |
| ZINC03313382 | 109 | 7583 | 7050 | 7928 | 21316 | 12498 | 9376 | 7170 | | 5818 | 1987 | 1825 | 8924 |
| ZINC06737368 | 194 | 13620 | 14739 | 3656 | 8620 | 12675 | 6931 | 3458 | 1291 | 5818 | 765 | 2144 | 10459 |
| ZINC03271868 | 259 | 17429 | 20935 | 11855 | 9359 | 13912 | 14650 | 6316 | 73 | | 5770 | | 5945 |
| ZINC04110856 | 267 | 12302 | 2321 | 8429 | 8861 | 14103 | 16660 | 9654 | | 4571 | | 2250 | 15512 |
| ZINC03429974 | 133 | 7368 | 3354 | 3907 | 16616 | 12987 | 13369 | 5239 | | 8595 | | | 15112 |

| INC ID | PRL3 | CDC14b | Pac-1 | Jsp-1 | CDC25b | VHZ | TMPD |
|---|---|---|---|---|---|---|---|
| ZINC05373221 | 12650 | 848 | 7111 | 4221 | 301 | 1063 | 2156 |
| ZINC06601214 | 13949 | 14844 | 14448 | 1181 | 14814 | 12311 | |
| ZINC03377116 | 7932 | 4695 | 2986 | 3188 | 14935 | 9394 | 12626 |
| ZINC00260730 | 18922 | 3790 | 21027 | 3400 | 17805 | 5129 | 16809 |
| ZINC04307500 | 6585 | 2976 | 14199 | 1102 | 9696 | 1821 | 13320 |
| ZINC00053046 | 13162 | 6378 | 11859 | 297 | 12043 | 2975 | 11863 |
| ZINC03313382 | 12938 | 7140 | 11223 | 2263 | 10808 | 4801 | |
| ZINC06737368 | 13299 | 5070 | 19725 | 4738 | 13012 | 5280 | 8847 |
| ZINC03271868 | 8436 | | 9059 | 2538 | 3581 | 5191 | 6665 |
| ZINC04110856 | 11032 | 350 | 14293 | 7311 | 9733 | 4990 | 3804 |
| ZINC03429974 | 11188 | 6209 | 2504 | 2425 | 12860 | 6951 | 3285 |

Figure 4B

Table 4. disparity list for new high potential inhibitors for SSH-2

| ZINC ID | VHR-SSH2 | VH3-SSH2 | PTEN-SSH2 | KAP-SSH2 | rVH6-SSH2 | mkp5-SSH2 | mkp4-SSH2 | VHY-SSH2 | MTMR2-SSH2 | VH1-SSH2 | DUSP18-SSH2 | CDC25a-SSH2 | PRL3-SSH2 | CDC14b-SSH2 |
|---|---|---|---|---|---|---|---|---|---|---|---|---|---|---|
| ZINC05373221 | 19671 | 5938 | 1610 | 19633 | 17775 | 15790 | 5749 | 14312 | 13271 | | 747 | 8742 | 12630 | 828 |
| ZINC06601214 | 5559 | 11652 | 3376 | 20522 | 13477 | 20127 | 7170 | 1435 | 7167 | 1817 | | 18887 | 13893 | 14788 |
| ZINC03377116 | 521 | 19406 | 2974 | 15715 | 13356 | 9424 | 6112 | 13948 | 6765 | | | 9966 | 7794 | 4557 |
| ZINC00260730 | 6955 | 3973 | 7513 | 6911 | | 11035 | 5694 | 866 | 4828 | 1908 | 2842 | 16783 | 18747 | 3615 |
| ZINC04307500 | 17478 | -50 | 5049 | 19741 | 8589 | 14133 | 6461 | 16628 | 5054 | 5058 | 873 | 15568 | 6406 | 2797 |
| ZINC00053046 | 2018 | 6037 | 5880 | 3850 | 14280 | 19701 | 16671 | 16838 | 3273 | 305 | 1038 | 12195 | 13108 | 6324 |
| ZINC03313382 | 7474 | 6941 | 7819 | 21207 | 12389 | 9267 | 7061 | | | 1878 | 1716 | 8815 | 12829 | 7031 |
| ZINC06737368 | 13426 | 14545 | 3462 | 8426 | 12481 | 6737 | 3264 | 1097 | 5624 | 571 | 1950 | 10265 | 13105 | 4876 |
| ZINC03271868 | 17170 | 20676 | 11596 | 9100 | 13653 | 14391 | 6057 | -186 | | 5511 | | 5686 | 8177 | |
| ZINC04110856 | 12035 | 2054 | 8162 | 8594 | 13836 | 16393 | 9387 | | 4304 | | 1983 | 15245 | 10765 | 83 |
| ZINC03429974 | 7235 | 3221 | 3774 | 16483 | 12854 | 13236 | 5106 | | 8462 | | | 14979 | 11055 | 6076 |

| ZINC ID | Pac1-SSH2 | Jsp1-SSH2 | CDC25b-SSH2 | VHZ-SSH2 | TMPD-SSH2 | Mean | Std Dev |
|---|---|---|---|---|---|---|---|
| ZINC05373221 | 7091 | 4201 | 281 | 1043 | 2136 | 9266.8 | 6931.8 |
| ZINC06601214 | 14392 | 1125 | 14758 | 12255 | | 10634.1 | 5729.9 |
| ZINC03377116 | 2848 | 3050 | 14797 | 9256 | 12488 | 8782.2 | 5678.5 |
| ZINC00260730 | 20852 | 3225 | 17630 | 4954 | 16634 | 8336.1 | 6576.3 |
| ZINC04307500 | 14020 | 923 | 9517 | 1642 | 13141 | 8721.5 | 6377.2 |
| ZINC00053046 | 11805 | 243 | 11989 | 2921 | 11809 | 8562.1 | 6387.1 |
| ZINC03313382 | 11114 | 2154 | 10699 | 4692 | | 8559.6 | 4971.0 |
| ZINC06737368 | 19531 | 4544 | 12818 | 5086 | 8653 | 8042.5 | 5541.3 |
| ZINC03271868 | 8800 | 2279 | 3322 | 4932 | 6406 | 9016.6 | 5915.2 |
| ZINC04110856 | 14026 | 7044 | 9466 | 4723 | 3537 | 8891.8 | 5060.8 |
| ZINC03429974 | 2371 | 2292 | 12727 | 6818 | 3152 | 8562.2 | 4936.0 |

SSH-2 (SLINGSHOT-2) INHIBITORS AND METHODS FOR MAKING AND USING THEM

RELATED APPLICATIONS

This application is a national phase application claiming benefit of priority under 35 U.S.C. §371 to Patent Convention Treaty (PCT) International Application Serial No: PCT/US2012/029267, filed Mar. 15, 2012, which claims benefit of priority to U.S. Provisional Patent Application Ser. No. 61/454,148, filed Mar. 18, 2011, which is expressly incorporated by reference herein in its entirety for all purposes.

GOVERNMENT RIGHTS

This invention was made with government support under grant HL085159 awarded by the National Institutes of Health (NIH) and grant OISE-0710726 awarded by the National Science Foundation (NSF). The government has certain rights in the invention.

TECHNICAL FIELD

This invention generally relates to biochemistry, medicine and drug discovery. In particular, in alternative embodiments, the invention provides compositions that inhibit the polypeptide SSH-2, or Slingshot-2 (SlingSHot-2), a phosphatase enzyme that regulates actin filaments, and methods for making and using them, including methods comprising administering compositions of the invention to regulate or modify actin filament polymerization by inhibiting SSH-2, where in one embodiment compositions of the invention inhibit or prevent F-actin depolymerization and severing. In alternative embodiments, compositions and methods of the invention are used to slow or inhibit cell motility and/or internal remodeling. In alternative embodiments, compositions and methods of the invention are used to slow or inhibit, or reverse, or ameliorate the progression of a cancer or a metastasis or other uncontrolled or unregulated cell growth, and/or Alzheimer's disease or dementia. In alternative embodiments, compositions of the invention are pharmaceutical compositions or formulations.

BACKGROUND

Cofilin is normally phosphorylated at serine 3; this phosphorylation prevents it from interacting with assembled F-actin filaments. The phosphatase SSH-2, or SlingSHot-2, dephosphorylates cofilin, allowing it to bind to F-actin and promote the disassembly of the actin filaments, as illustrated in FIG. 1.

SUMMARY

In alternative embodiments, the invention provides pharmaceutical compounds, formulations or compositions or compounds comprising or consisting of: 3-[(4,5-dimethoxy-3-oxo-1Hisobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog or derivative, or stereoisomer or bioisostere, thereof.

In alternative embodiments, the invention provides pharmaceutical compounds, formulations or compositions or compounds selected from the group consisting of (or having a structure comprising):

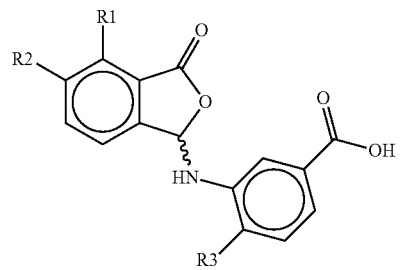

wherein R1 and R2 can be any alkoxy group, including methoxy-, ethox-, butoxy-, etc.) or having a longer alkyl or alkene group, or any combination thereof, and R3 can be any alkyl group, including a methyl, ethyl, propyl or butyl or longer alkyl or alkene group, or any combination thereof;

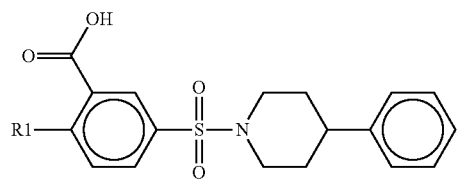

wherein R1 can be any alkoxy group, including methoxy, ethox, butoxy, etc.) or having a longer alkyl or alkene group, or any combination thereof;

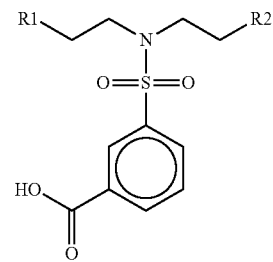

wherein R1 and R2 can be any alkoxy group, including methoxy, ethox, butoxy, etc.) or having a longer alkyl or alkene group, or any combination thereof;

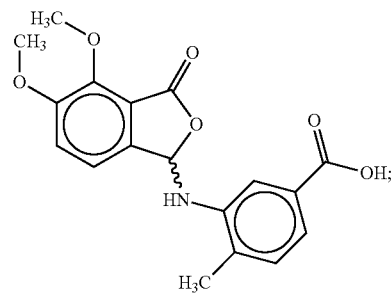

(ZINC 05375291)

-continued (ZINC 04107594)

(ZINC 02655717)

wherein R1 can be any alkyl group, including a methyl, ethyl, propyl or butyl or longer alkyl or alkene group, or any combination thereof;

wherein R1 and R2 can be any alkyl group, including a methyl, ethyl, propyl or butyl or longer alkyl or alkene group, or any combination thereof;

wherein R1, R2, R3, R4, and R5 can be any alkyl group, including a methyl, ethyl, propyl or butyl or longer alkyl or alkene group, or any combination thereof;
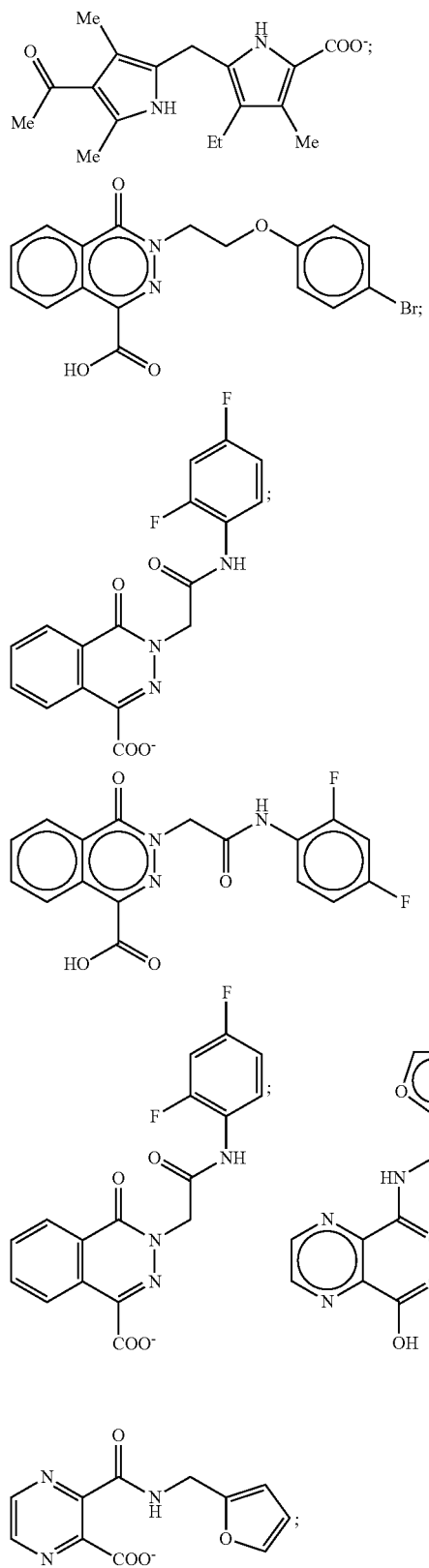
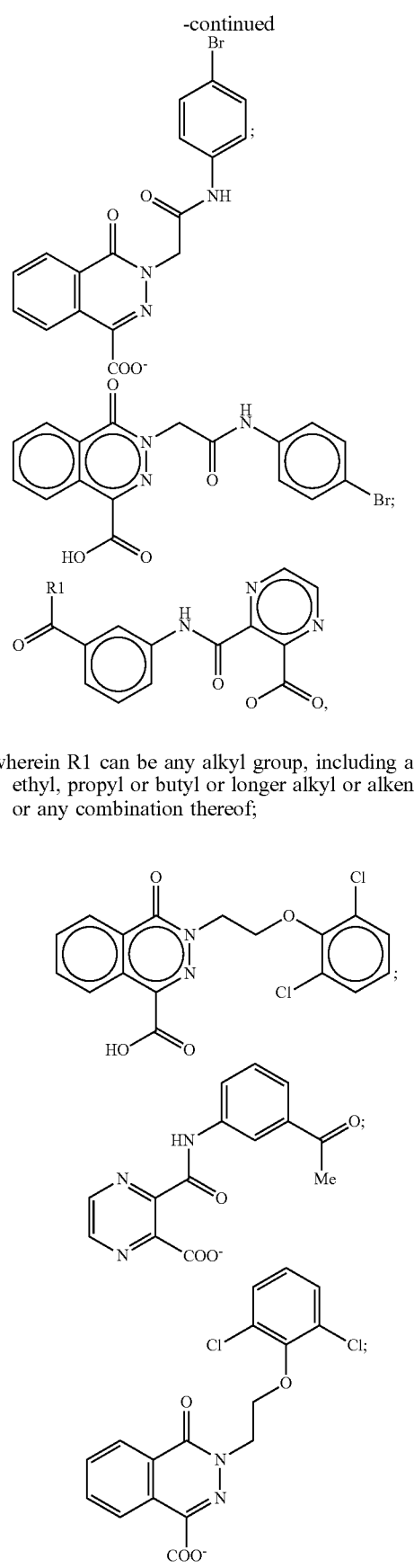
wherein R1 can be any alkyl group, including a methyl, ethyl, propyl or butyl or longer alkyl or alkene group, or any combination thereof;

any combination thereof, and any analog or derivative, or stereoisomer or bioisostere, thereof.

In alternative embodiments, the pharmaceutical compounds, formulations or compositions of the invention are formulated for enteral or parenteral administration; or formulated as a pill, tablet, geltab, powder, liquid, gel, aerosol or implant.

In alternative embodiments, the invention provides methods for inhibiting or slowing the dephosphorylating of a cofilin in a cell, comprising:
(i) (a) providing at least one pharmaceutical compound, formulation or composition of the invention, or a composition comprising or consisting of:
3-[(4,5-dimethoxy-3-oxo-1Hisobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog or derivative, or stereoisomer or bioisostere, thereof; and
(b) contacting the at least one pharmaceutical compound, formulation or composition of (a) with a SSH-2 or SlingShot-2 polypeptide in the cell in an amount sufficient to inhibit or slow the dephosphorylating of the cofilin; or
(ii) the method of (i), wherein the contacting of the at least one pharmaceutical compound, formulation or composition with the SSH-2 is in vitro, ex vivo or in vivo.

In alternative embodiments, the invention provides methods for inhibiting or preventing the binding of a cofilin to an F-actin, comprising:
(i) (a) providing at least one pharmaceutical compound, formulation or composition of the invention, or a composition comprising or consisting of:
3-[(4,5-dimethoxy-3-oxo-1Hisobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog or derivative, or stereoisomer or bioisostere, thereof; and
(b) contacting the at least one pharmaceutical compound, formulation or composition of (a) with a SSH-2 or SlingShot-2 polypeptide in the cell in an amount sufficient to inhibit or slow the dephosphorylating of the cofilin, thereby inhibiting or preventing the binding of a cofilin to an F-actin; or
(ii) the method of (i), wherein the contacting of the at least one compound or composition with the SSH-2 is in vitro, ex vivo or in vivo.

In alternative embodiments, the invention provides methods for stabilizing F-actin polymers, actin filaments, or actin-comprising microtubules, in a cell, comprising:
(i) (a) providing at least one pharmaceutical compound, formulation or composition of the invention, or a composition comprising or consisting of:
3-[(4,5-dimethoxy-3-oxo-1Hisobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog or derivative, or stereoisomer or bioisostere, thereof; and
(b) administering the at least one pharmaceutical compound, formulation or composition of (a) to the cell (or, inserting the pharmaceutical compound or composition into the cell) in an amount sufficient to stabilize the F-actin polymer, actin filament, or actin-comprising microtubule; or
(ii) the method of (i), wherein the administering of the at least one pharmaceutical compound, formulation or composition to the cell is in vitro, ex vivo or in vivo.

In alternative embodiments, the invention provides methods for decreasing cell motility, comprising:
(i) (a) providing at least one pharmaceutical compound, formulation or composition of the invention, or a composition comprising or consisting of:
3-[(4,5-dimethoxy-3-oxo-1Hisobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog, or stereoisomer or bioisostere, or derivative thereof; and
(b) administering the at least one pharmaceutical compound, formulation or composition of (a) to the cell (or, inserting the pharmaceutical compound or composition into the cell) in an amount sufficient to decrease the cell's motility; or
(ii) the method of (i), wherein the administering of the pharmaceutical compound, formulation or composition to the cell is in vitro, ex vivo or in vivo.

In alternative embodiments, the invention provides methods for ameliorating a disease or condition responsive to inhibiting or decreasing cell motility and/or stabilizing F-actin polymers, actin filaments, or actin-comprising microtubules in a cell, comprising:
(i) (a) providing at least one pharmaceutical compound, formulation or composition of the invention, or a composition comprising or consisting of:
3-[(4,5-dimethoxy-3-oxo-1Hisobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog or derivative thereof; and
(b) administering the at least one pharmaceutical compound, formulation or composition of (a) to an individual in need thereof in an amount sufficient to inhibit or decrease cell motility and/or stabilize F-actin polymers, actin filaments, or actin-comprising microtubules; or
(ii) the method of (i), wherein disease or condition ameliorated is cancer, a metastasis and/or Alzheimer's disease.

In alternative embodiments, the invention provides methods for decreasing or inhibiting cell growth, comprising:
(i) (a) providing at least one pharmaceutical compound, formulation or composition of the invention, or a composition comprising or consisting of:
3-[(4,5-dimethoxy-3-oxo-1Hisobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog or derivative thereof; and
(b) administering the at least one pharmaceutical compound, formulation or composition of (a) to the cell (or, inserting the pharmaceutical compound or composition into the cell) in an amount sufficient to decrease or inhibit cell growth; or
(ii) the method of (i), wherein the administering of the at least one pharmaceutical compound, formulation or composition to the cell is in vitro, ex vivo or in vivo.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

Figures are described in detail herein.

FIG. 1 illustrates exemplary mechanisms of action for the compositions and methods of this invention; illustrating that phosphatase SSH-2, or SlingSHot-2, dephosphorylates cofilin, allowing it to bind to F-actin and promote the disassembly of the actin filaments.

FIGS. 4A and 4B illustrate SSH-2 specificity of exemplary compounds of the invention, as described e.g. in Example 1, below.

FIG. 5(A) illustrates an immunoblot of cells treated with the exemplary compound of the invention ZINC4307500; in FIG. 5(A), cells treated with ZINC4307500 show an increase in p-cofilin levels at 100 μM and 10 μM; and, FIG. 5(B) graphically illustrates data summarizing the levels of p-cofilin over 5 experimental repeats as described e.g. in Example 1, below.

Like reference symbols in the various drawings indicate like elements.

Figure 1:
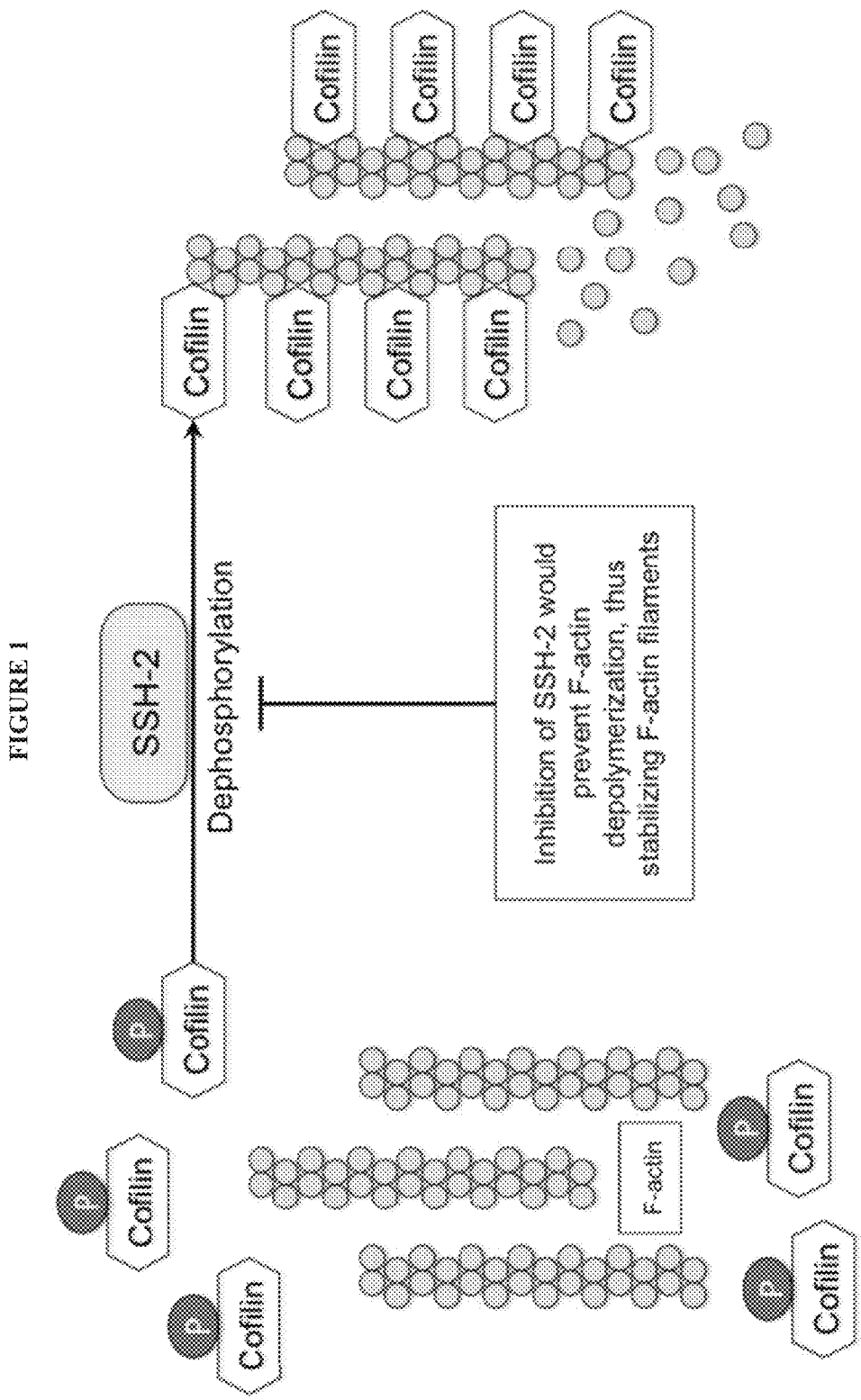
FIG. 1: while the invention is not limited by any particular mechanism of action.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

This invention for the first time provides inhibitors of phosphatases that regulate actin filaments. In particular, in alternative embodiments, the invention provides compositions that inhibit the polypeptide SSH-2, or SlingSHot-2, a phosphatase enzyme that regulates actin filaments, and methods for making and using them, including methods comprising administering compositions of the invention to regulate or modify actin filament polymerization by inhibiting SSH-2 enzyme activity (i.e., inhibit dephosphorylation), where in one embodiment compositions of the invention inhibit or prevent F-actin depolymerization and severing.

Compositions and methods of the invention, by inhibiting SSH-2, can be used to control cell growth and movement. While the invention is not limited by any particular mechanism of action, in one embodiment, compositions and methods of the invention, by inhibiting SSH-2, are used to control cell growth and movement by inhibiting or preventing dephosphorylation of cofilin at serine 3, thereby inhibiting or preventing cofilin to bind to F-actin and stimulate F-actin depolymerization and severing (thus depolymerization and severing are inhibited or prevented. In alternative embodiments, compositions and methods of the invention inhibit the SSH-2 enzyme, resulting in inhibiting or preventing subsequent F-actin depolymerization; severing is also inhibited or prevented, and cell motility and/or internal remodeling are inhibited or prevented Because SSH-2 contributes to the progression of cancer and Alzheimer's disease or dementia, compositions and methods of the invention, by inhibiting SSH-2, can be used to slow or inhibit, or reverse, or ameliorate (decrease the symptoms of, slow the onset or progression of, reverse, or prevent) the progression of a cancer or a metastasis or other uncontrolled or unregulated cell growth, and/or Alzheimer's disease or dementia.

Bioisosteres of Compounds of the Invention

In alternative embodiments, the invention also provides bioisosteres of compounds of the invention, e.g., compounds having a structure as set forth herein. In alternative embodiments, bioisosteres of the invention are compounds of the invention comprising one or more substituent and/or group replacements with a substituent and/or group having substantially similar physical or chemical properties which produce substantially similar biological properties to a compound of the invention, or stereoisomer, racemer or isomer thereof. In one embodiment, the purpose of exchanging one bioisostere for another is to enhance the desired biological or physical properties of a compound without making significant changes in chemical structures.

For example, in one embodiment, bioisosteres of compounds of the invention are made by replacing one or more hydrogen atom(s) with one or more fluorine atom(s), e.g., at a site of metabolic oxidation; this may prevent metabolism (catabolism) from taking place. Because the fluorine atom is similar in size to the hydrogen atom the overall topology of the molecule is not significantly affected, leaving the desired biological activity unaffected. However, with a blocked pathway for metabolism, the molecule may have a longer half-life or be less toxic, and the like.

Formulations and Pharmaceutical Compositions

In alternative embodiments, the invention provides compositions for use in in vivo, in vitro or ex vivo methods for inhibiting an SSH-2 enzyme, resulting in inhibiting or preventing subsequent F-actin depolymerization; and also for decreasing or inhibiting cell growth comprising administering to a cell or contacting a cell with a compound or a formulation or a pharmaceutical composition of the invention in vitro, ex vivo or in vivo. In alternative embodiments, the compositions of the invention are used in in vivo, in vitro or ex vivo methods for treating, preventing and/or ameliorating a disease or condition that can be responsive to or ameliorated by decreasing or inhibiting cell growth, e.g., a pathological, uncontrolled or unwanted cell growth, e.g., a cancer or a metastases, or any disease or condition or infection having a hyperproliferative cell growth component. In alternative embodiments, the compositions of the invention are used for ameliorating or preventing an inflammatory disease or condition that can be ameliorated by decreasing or inhibiting cell growth or proliferation. In alternative embodiments, the compositions of the invention are used for ameliorating or preventing the progression of cancer, metastases and Alzheimer's disease.

In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice this invention can be in forms such as tablets, pills, powders, capsules, liquids, gels, syrups, slurries, suspensions, etc., suitable for in vivo, in vitro or ex vivo applications.

In practicing this invention, the compounds (e.g., formulations) of the invention can comprise a solution of compositions of the invention disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations of the invention can be delivered by the use of liposomes. By using liposomes, particularly where the liposome surface carries ligands specific for target cells (e.g., a cancer cell), or are otherwise preferentially directed to a specific tissue or organ type, one can focus the delivery of the active agent into a target cells in an in vivo, in vitro or ex vivo application.

Nanoparticles, Nanolipoparticles and Liposomes

The invention also provides nanoparticles, nanolipoparticles, vesicles and liposomal membranes comprising compounds used to practice the methods of this invention, e.g., to deliver compositions of the invention to mammalian cells in vivo, in vitro or ex vivo. In alternative embodiments, these compositions are designed to target specific molecules, including biologic molecules, such as polypeptides, including cell surface polypeptides, e.g., for targeting a desired cell type, e.g., a cancer cell, a stem cell, a cancer stem cell, a mammalian cell, an epithelial cell, an intestinal epithelial cell, or a mucosal cell and the like.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice this invention.

Liposomes can be made using any method, e.g., as described in Park, et al., U.S. Pat. Pub. No. 20070042031, including method of producing a liposome by encapsulating an active agent (e.g., a composition of the invention), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound used to practice this invention to a desired cell type (e.g., a cancer cell), as described e.g., in U.S. Pat. Pub. No. 20070110798.

The invention also provides nanoparticles comprising used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice this invention to mammalian cells in vivo, in vitro or ex vivo, as described, e.g., in U.S. Pat. Pub. No. 20050136121.

Delivery Vehicles

In alternative embodiments, any delivery vehicle can be used to practice the methods or used to practice this invention, e.g., to deliver compositions of the invention to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice this invention, e.g. as described, e.g., in U.S. Pat. Pub. No. 20040151766.

In one embodiment, a composition used to practice this invention can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Dosaging

The pharmaceutical compositions and formulations of the invention can be administered for prophylactic and/or therapeutic treatments. In therapeutic applications, compositions are administered to a subject already suffering from a cancer, disease, condition, infection or disease in an amount sufficient to cure, alleviate or partially arrest the clinical manifestations of the cancer, disease, condition, infection or disease and its complications (a "therapeutically effective amount"). For example, in alternative embodiments, pharmaceutical compositions and formulations of the invention are administered in an amount sufficient to treat, prevent and/or ameliorate a disease or condition that can be ameliorated by decreasing or inhibiting cell growth, e.g., a cancer or metastasis, or any unwanted cell growth.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, alternative exemplary pharmaceutical formulations for oral administration of compositions used to practice the invention are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating cancer, and inflammatory disease and the like. For example, the methods and/or compositions and formulations of the invention can be co-formulated with and/or co-administered with, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Products of Manufacture, Kits

The invention also provides products of manufacture, kits and pharmaceuticals for practicing the methods of this invention. In alternative embodiments, the invention provides products of manufacture, kits and/or pharmaceuticals comprising all the components needed to practice a method of the invention, including at least one compound of the invention, and/or instructions for practicing a method of this invention.

Synthesis of Compounds of the Invention

Compounds of the invention can be synthesized using any technique known in the art, e.g., using standard procedures and chemical transformations, methods and procedures as described, for example, in standard references such as *Fiesers' Reagents for Organic Synthesis*, John Wiley and Sons, New York, N.Y., 2002; *Organic Reactions*, vols. 1-83, John Wiley and Sons, New York, N.Y., 2006; March J. and Smith M., *Advanced Organic Chemistry*, 6th ed., John Wiley and Sons, New York, N.Y.; and Larock R. C., *Comprehensive Organic Transformations*, Wiley-VCH Publishers, New York, 1999.

The invention will be further described with reference to the examples described herein; however, it is to be understood that the invention is not limited to such examples.

EXAMPLES

Example 1

Exemplary Compositions of the Invention

This example describes the identification and structure of exemplary compositions of the invention.

Using a molecular docking simulation software DOCK 6.0™ (UCSF Molecular Design Institute, University of California—San Francisco (UCSF), San Francisco, Calif.), open-source chemical database ZINC™ (the Shoichet Laboratory in the Department of Pharmaceutical Chemistry at UCSF, San Francisco, Calif.) were virtually screened to determine the binding affinities to five dual specificity (tyrosine/serine) phosphatases (DSPs), specifically SSH-2, VHR (DUS3), VH3 (DUSS), PTEN (phosphatase and tensin homolog), and KAP (kinase (Cdk)-associated protein phosphatase).

Figure 2:
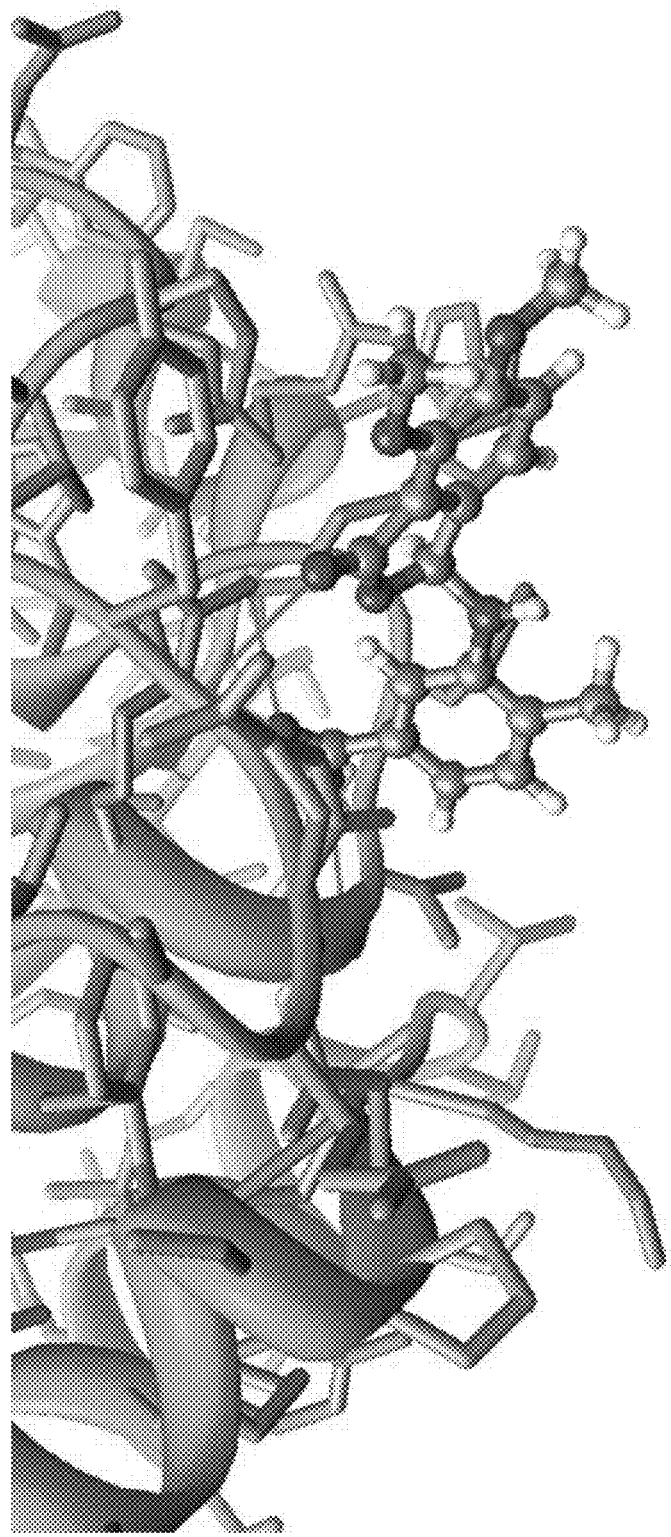
FIG. 2 is an illustration showing the interaction between the catalytic site of SSH-2 and the compound ZINC ID 05375291, or 3-[(4,5-dimethoxy-3-oxo-1,3-dihydro-2-benzofuran-1-yl)amino]-4-methylbenzoic acid.
Figure 3A:
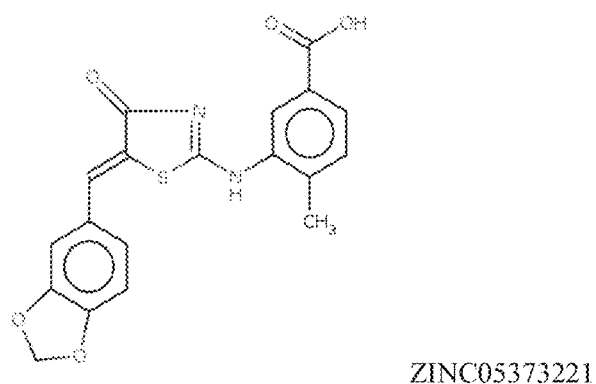
FIGS. 3A, 3B, 3C, 3D and 3E illustrate exemplary compounds of the invention, and these compounds have specificity for SSH-2: as shown in Tables 3 and 4, as illustrated in FIGS. 4A and 4B respectively, e.g., the exemplary ZINC 06601214 and ZINC 03377116 compounds of this invention, as described e.g. in Example 1, below.
Figure 3A:
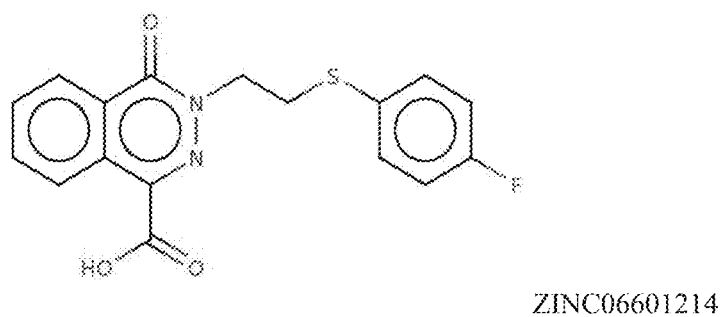
Figure 3A:
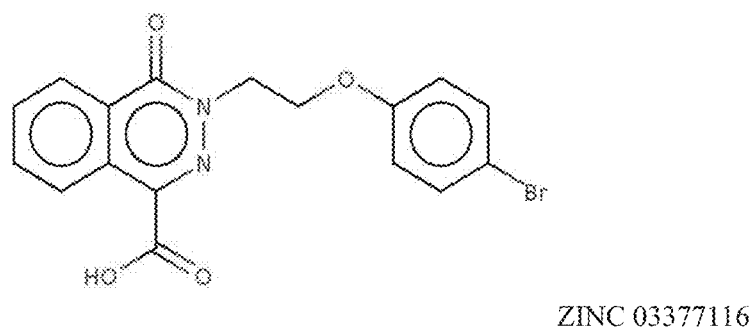
Figure 3B:
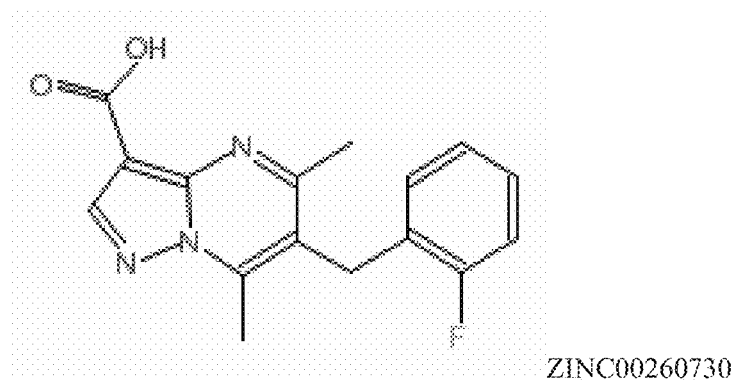
Figure 3B:
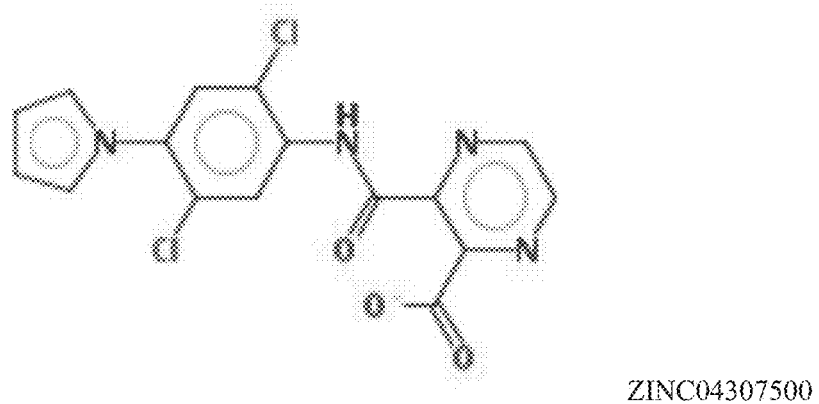
Figure 3C:
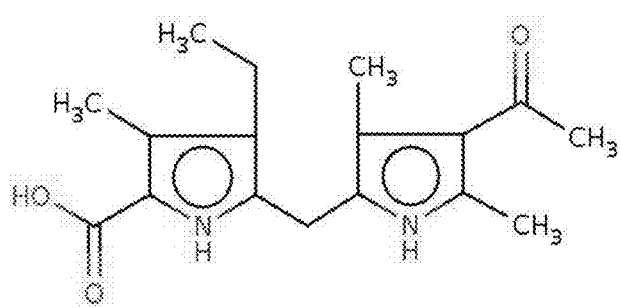
Figure 3C:
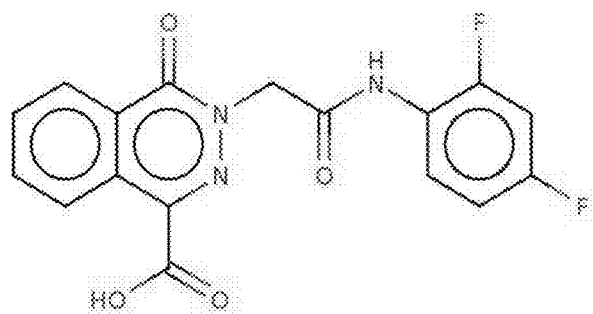
Figure 3D:
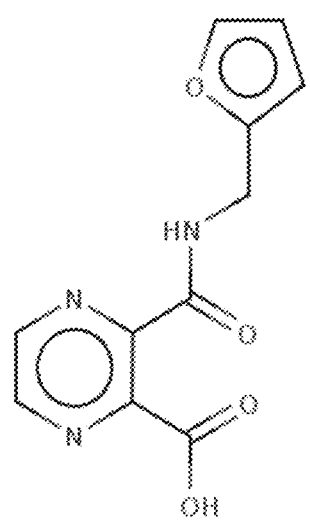
Figure 3D:
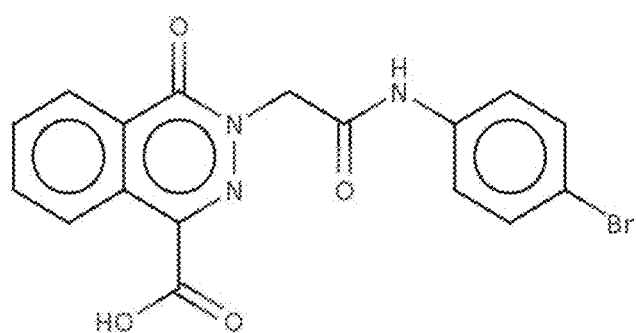
Figure 3E:
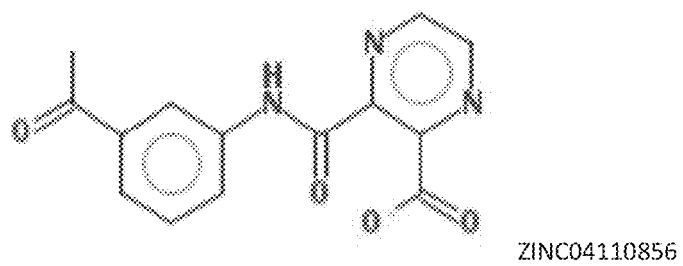
Figure 3E:
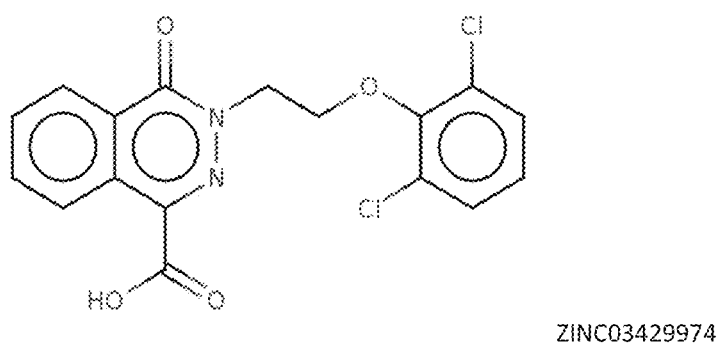

Among the best 100 SSH-2 binding compounds, (3-[(4, 5-dimethoxy-3-oxo-1H-isobenzofuran-1-yl)amino]-4-methyl-benzoic acid, ZINC ID 05375291) shows the highest affinity for SSH-2, but lowest affinity for the other DSPs. FIG. 2 is an illustration showing the interaction between the catalytic site of SSH-2 and the compound ZINC ID 05375291, or 3-[(4,5-dimethoxy-3-oxo-1,3-dihydro-2-benzofuran-1-yl)amino]-4-methylbenzoic acid, with hydrogen bonds highlighted in green; FIG. 2 illustrates 3-[(4,5-dimethoxy-3-oxo-1Hisobenzofuran-1-yl)amino]-4-methylbenzoic acid (ZINC ID 05375291) bound to the catalytic site of SSH-2.

Table 1, below, lists three (3) compounds with rankings for their affinity and specificity to SSH-2. These SSH-2 inhibitors of the invention can be used as novel therapeutics for cancer, metastases, Alzheimer's disease and other diseases or conditions responsive to inhibition of SSH-2.

TABLE 1

List of high potential specific inhibitors for SSH-2 and their consensus

| ZINC ID | Consensus Rank | | | | |
|---|---|---|---|---|---|
| | SSH2 | VHR | VH3 | PTEN | KAP |
| 05375291 | 66 | 19335 | 18113 | 3448 | 6718 |
| 04107594 | 16 | 19810 | 1743 | 4201 | 633 |
| 02655717 | 63 | 12663 | 256 | 208 | 935 |

TABLE 2

The ranking disparity of each DSP with SSH-2 with the mean and std. dev.

| ZINC ID | Disparity | | | | | |
|---|---|---|---|---|---|---|
| | VHR-SSH2 | VH3-SSH2 | PTEN-SSH2 | KAP-SSH2 | Mean | Std. Dev. |
| 05375291 | 19269 | 18047 | 3382 | 6652 | 11837 | 8003 |
| 04107594 | 19794 | 1727 | 4185 | 617 | 6580 | 8934 |
| 02655717 | 12600 | 193 | 145 | 872 | 3452 | 6107 |

| ZINC ID | |
|---|---|
| ZINC ID 05375291 3-[(4,5dimethoxy-3-oxo-1,3-dihydro-2-benzofuran-1-yl)amino]-4-methylbenzoic acid | 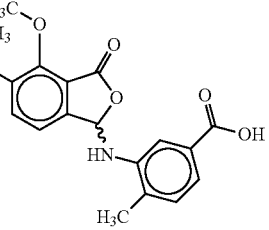 |
| ZINC ID 04107594 2-ethoxy-5-(4-phenylpiperidine-1-sulfonyl) benzoic acid | 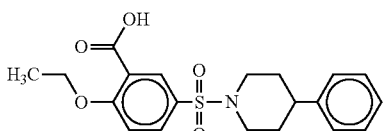 |
| ZINC ID 02655717 3-[bis(2-methoxyethyl) sulfamoyl] benzoic acid | 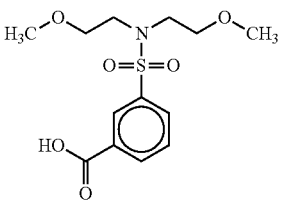 |

Computer model simulations used the open-source chemical database (ZINC, UC San Francisco) in virtual screenings and a small list of potential specific inhibitors, as shown in Table 1. The consensus rank is found by adding the energy and AMBER score rankings of a compound to a receptor. The difference in consensus ranking of each DSP with SSH-2 is shown in Table 2 as disparity scores. The mean and standard deviation are the statistics of the disparity. These results show a low consensus rank that indicates the compound binds tightly to SSH-2 and a high consensus rank for each of the other four DSPs that suggests weak binding. The disparity gives the specific difference between each DSP with SSH-2 and the mean shows the overall difference. A large mean and a large standard deviation suggest large variation in binding of the compound to each DSP and most importantly high specificity for SSH-2.

The results from five DSP member virtual screenings, specifically SSH-2, VHR, VH3, PTEN and KAP, suggest that 3-[(4,5-dimethoxy-3-oxo-1H-isobenzofuran-1-yl) amino]-4-methyl-benzoic acid (ZINC ID 05375291) shows the highest affinity for SSH-2, but the lowest affinity for the other DSPs, among the 100 best SSH-2 binding compounds.

Virtual screening with the other DSP family members was done to determine how specific the binding of this compound is to SSH-2; 20 of 24 additional DSPs with known three-dimensional structures as determined by x-ray crystallography were completed. These data show that these three compounds have high affinity for other members of the DSP family. Specifically, ZINC 05375291 and ZINC 04107594 bind to DUSP18 with high affinity (consensus rank 614, and 94 respectively) and ZINC 02655717 bind to VH1 with high affinity (consensus rank 67). These rankings suggest that these three compounds would not likely be specific for SSH-2.

Data shows that eleven new compounds, exemplary compounds of the invention as illustrated in FIGS. 3A, 3B, 3C, 3D and 3E, have specificity for SSH-2: as shown in Tables 3 and 4 (FIGS. 4A and 4B respectively), e.g., the exemplary ZINC 06601214 and ZINC 03377116 compounds of this invention. Two exemplary compounds (ZINC 06601214 and ZINC 03377116) have very similar chemical structures; see FIGS. 3A, 3B, 3C, 3D and 3E.

In alternative embodiments, exemplary compounds of the invention also include ZINC 06601214, ZINC 03377116, ZINC 03313382, ZINC 03271868, and ZINC 03429974. These five compounds have very similar chemical structures.

In Vitro Verification

The exemplary compound of the invention ZINC04307500 was demonstrated to inhibit SSH-2.

HeLa cells were used for the in vitro verification portion of the study. Cells were first seeded onto 2 cm diameter plates and allowed to attach and proliferate for 24 hours. Compounds dissolved in dimethyl sulfoxide (DMSO) were applied the next day at 100 μm, 10 μm, 1 μm, 0.1 μm, and 0.01 μm concentrations and a DMSO vehicle control was used. The cells were incubated for a period of 24 hours and lysed (1% Triton X-100/10 mM Tris base/50 mM NaCl/30 mM Na pyrophosphate/50 mM NaF) in the presence of protease inhibitors and 1 mM $Na_3VO_4$. (as described e.g., in Fauman (1996) Trends in biochemical sciences 21(11):413-417). The lysate was centrifuged at 10,000 rpm for 15 minutes at 4° C. The total protein concentration of the supernatant was measured and 10 μg of the total protein was used for immunoblotting. Actin levels were also probed to ensure equal loading and phosphocofilin was probed to determine the inhibitory effects of the applied compound on SSH-2. Ratio of phosphocofilin to actin was determined at each applied concentration and expressed as mean±SEM. Statistical analyses were performed using analysis of variance followed by a Student-Neuman-Keuls post hoc test between samples and control, and probability values (p) for significance were calculated with $p<0.05$ being considered as statically significant.

Figure 5:
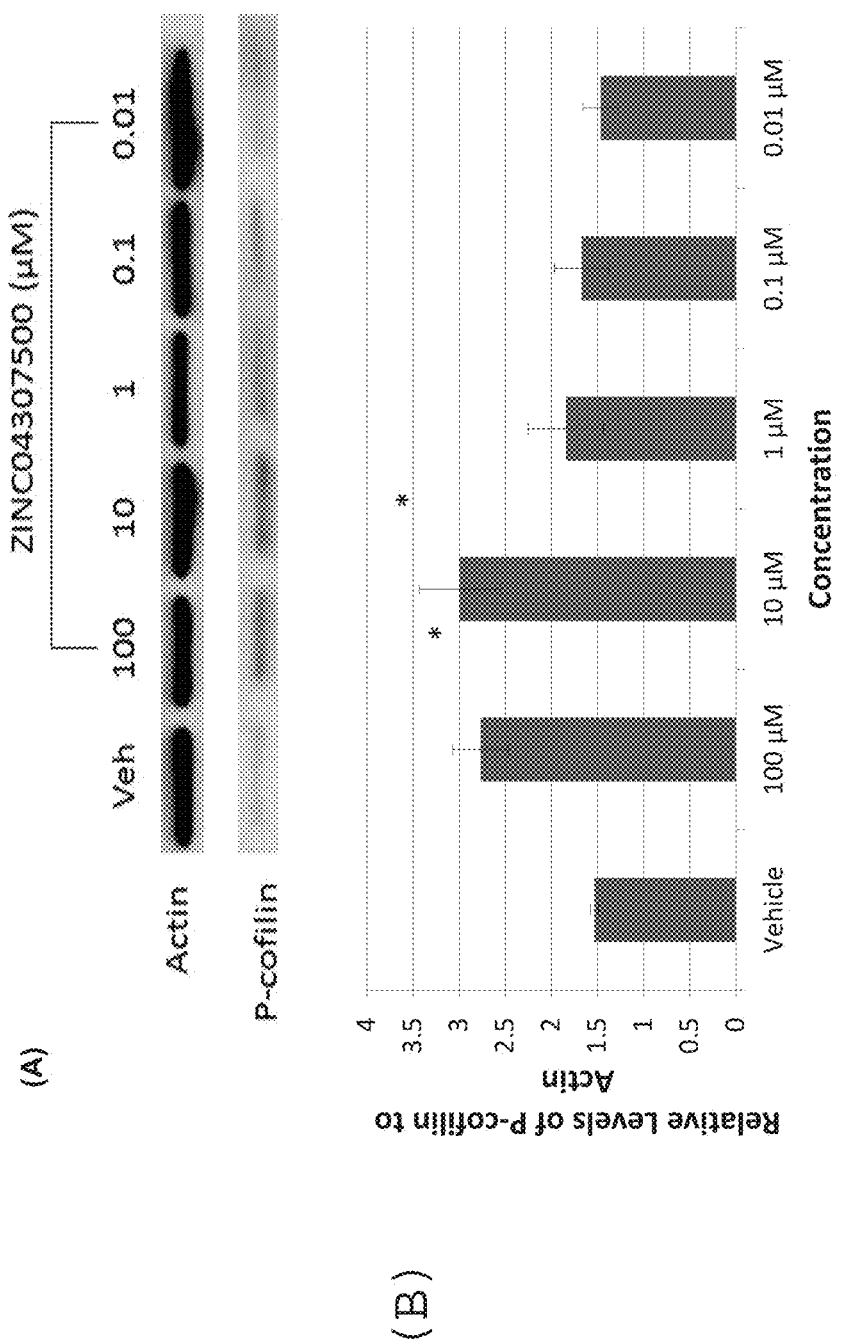
FIG. 5.

As shown in FIG. 5A, cells treated with ZINC04307500 revealed an increase in phosphocofilin (p-cofilin) in comparison to vehicle control. FIG. 5A illustrates a representative example of an immunoblot of cell lysate treated with ZINC04307500. FIG. 5B illustrates a graphic summarization of the results, where n=5 experiments are summarized. There is a significant increase in p-cofilin levels in cells treated with 100 μM and 10 μM of the exemplary compound of the invention ZINC04307500 in comparison to control (p<0.05), demonstrating that SSH-2 is inhibited by the exemplary compound of the invention ZINC04307500.

FIG. 5(A) illustrates an immunoblot of cells treated with the exemplary compound of the invention ZINC04307500. In FIG. 5(A), cells treated with ZINC04307500 show an increase in p-cofilin levels at 100 μM and 10 μM. FIG. 5(B) graphically illustrates data summarizing the levels of p-cofilin over 5 experimental repeats. Significant increase in p-cofilin level is observed in cells treated with 100 μM and 10 μM of ZINC04307500 in comparison to vehicle. This data demonstrates that SSH-2 is inhibited by the exemplary compound of the invention ZINC04307500. In FIG. 5(B), * indicates statistically significant difference in p-cofilin level compared to vehicle p<0.05.

A number of embodiments of the invention have been described. Nevertheless, it will be understood that various modifications may be made without departing from the spirit and scope of the invention. Accordingly, other embodiments are within the scope of the following claims.

What is claimed is:

1. A pharmaceutical compound, a formulation, or a composition comprising: 3-[(4,5-dimethoxy-3-oxo-1H-isobenzofuran-1-yl)amino]-4-methylbenzoic acid; 2-ethoxy-5-(4-phenylpiperidine-1-sulfonyl)benzoic acid; 3-[bis(2-methoxyethyl)sulfamoyl]benzoic acid; or any combination thereof, or any analog or derivative thereof, or a stereoisomer or a bioisostere thereof.

2. A pharmaceutical compound, a formulation or a composition selected from the group consisting of:

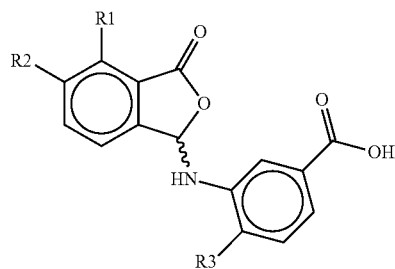

wherein R1 and R2 can be any alkoxy group, methoxy-group, ethoxy- group, butoxy- group, or a group having a longer alkyl or alkene group; or any combination thereof, and R3 can be any alkyl group, including a methyl, ethyl, propyl or butyl or longer alkyl or alkene group, or any combination thereof;

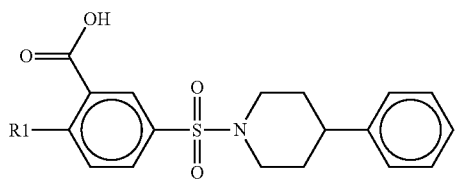

wherein R1 can be any alkoxy group, including methoxy, ethoxy, butoxy, etc.) or having a longer alkyl or alkene group, or any combination thereof;

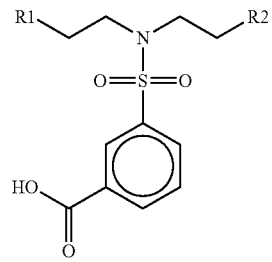

wherein R1 and R2 can be any alkoxy group, including methoxy, ethoxy, butoxy, etc.) or having a longer alkyl or alkene group, or any combination thereof;

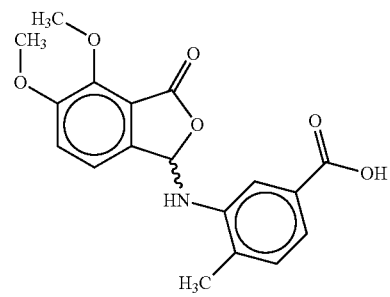

3-[(4,5dimethoxy-3-oxo-1,3-dihydro-2-benzofuran-1-yl)amino]-4-methylbenzoic acid;

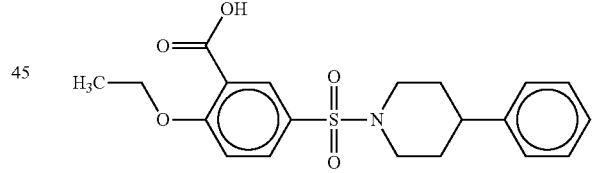

2-ethoxy-5-(4-phenylpiperidine-1-sulfonyl)benzoic acid;

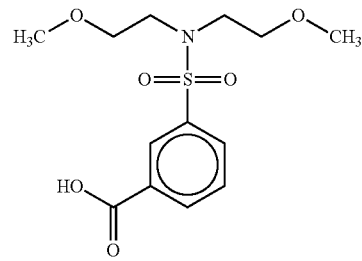

3-[bis(2-methoxyethyl)sulfamoyl]benzoic acid;

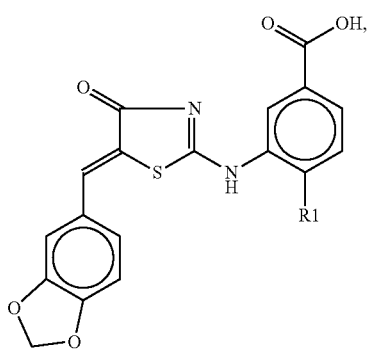

wherein R1 can be any alkyl group, including a methyl, ethyl, propyl or butyl or longer alkyl or alkene group, or any combination thereof;

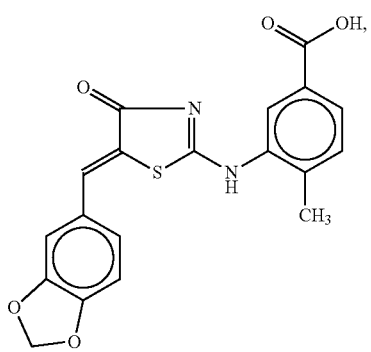

ZINC 05373221 wherein Me is a methyl group and COO⁻ is a carboxy group;

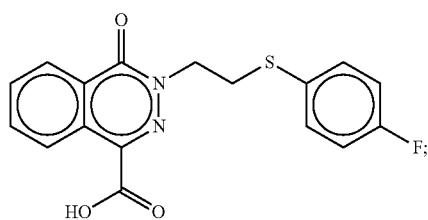

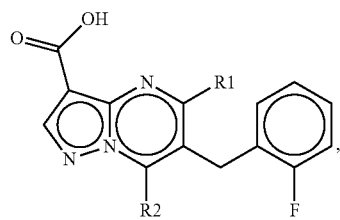

wherein R1 and R2 can be any alkyl group, including a methyl, ethyl, propyl or butyl or longer alkyl or alkene group, or any combination thereof;

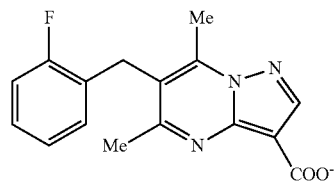

wherein Me is a methyl group and COO⁻ is a carboxy group;

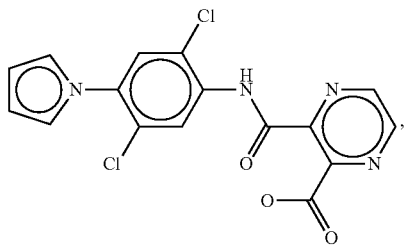

wherein COO⁻ is a carboxy group;

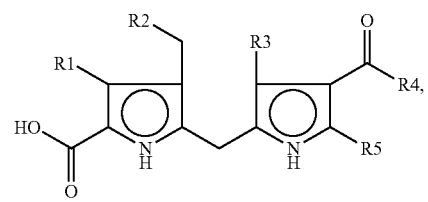

wherein R1, R2, R3, R4, and R5 can be any alkyl group, including a methyl, ethyl, propyl or butyl or longer alkyl or alkene group, or any combination thereof;

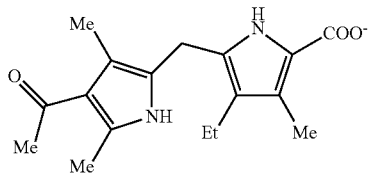

wherein Me is a methyl group and Et is an ethyl group;

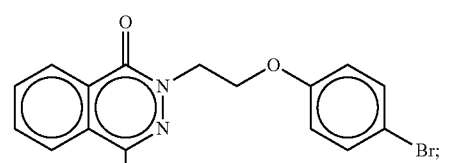

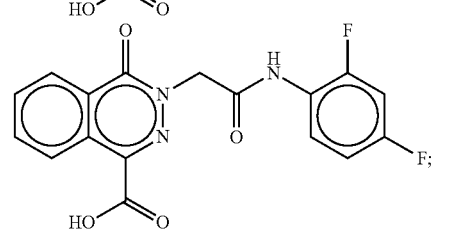

-continued

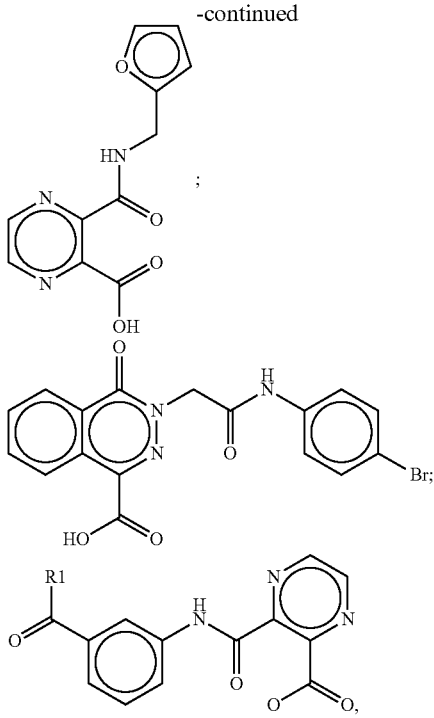

wherein R1 can be any alkyl group, including a methyl, ethyl, propyl or butyl or longer alkyl or alkene group, or any combination thereof

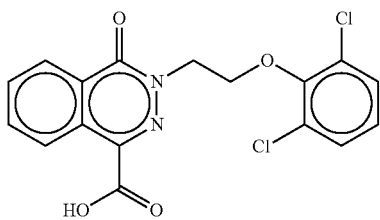

3-[2-(2,6-dichlorophenoxy)ethyl]-4-oxophthalazine-1-carboxylate; ZINC03429974,

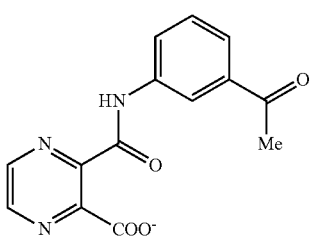

ZINC 04110856 wherein Me is a methyl group and COO⁻ is a carboxy group; any combination thereof, and any analog or derivative, or stereoisomer or bioisostere thereof.

3. The pharmaceutical compound, formulation or composition of claim 1, formulated for enteral or parenteral administration; or formulated as a pill, tablet, geltab, powder, liquid, gel, aerosol or implant.

4. The pharmaceutical compound, formulation or composition of claim 2, formulated for enteral or parenteral administration; or formulated as a pill, tablet, geltab, powder, liquid, gel, aerosol or implant.

5. A method for inhibiting or slowing the dephosphorylating of a cofilin, comprising:

providing a pharmaceutical formulation or composition compound a compound ZINC04307500 having the structure

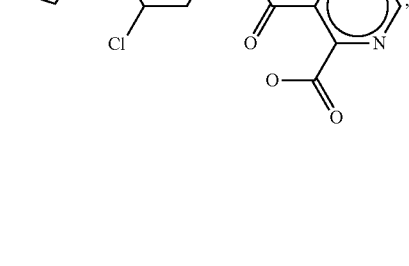

and (b) contacting the pharmaceutical compound, formulation or composition of (a) with a SSH-2 or SlingShot-2 polypeptide in an amount sufficient to inhibit or slow the dephosphorylating of the cofilin.

6. A method for inhibiting or slowing the dephosphorylating of a cofilin in a cell, comprising:

(i) (a) providing a pharmaceutical, formulation or composition comprising a compound ZINC04307500 having the structure:

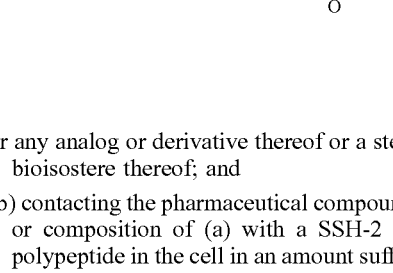

or any analog or derivative thereof or a stereoisomer or a bioisostere thereof; and (b) contacting the pharmaceutical compound, formulation or composition of (a) with a SSH-2 or SlingShot-2 polypeptide in the cell in an amount sufficient to inhibit or slow the dephosphorylating of the cofilin; or (ii) the method of (i), wherein the contacting of the compound or composition with the SSH-2 or SlingShot-2 polypeptide is in vitro, ex vivo or in vivo.

7. A method for inhibiting or preventing the binding of a cofilin to an F-actin, comprising:
(i) providing a pharmaceutical, formulation or composition
comprising a compound ZINC04307500 having the structure:

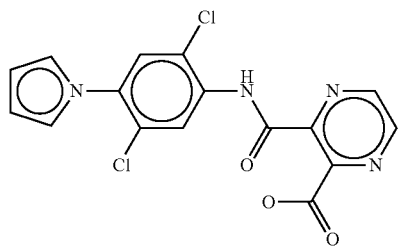

or any analog or derivative thereof or a stereoisomer or a bioisostere thereof; and
(b) contacting the pharmaceutical compound, formulation or composition of (a) with a SSH-2 or SlingShot-2 polypeptide in the cell in an amount sufficient to inhibit or slow the dephosphorylating of the cofilin, thereby inhibiting or preventing the binding of a cofilin to an F-actin; or
(ii) the method of (i), wherein the contacting of the compound or composition with the SSH-2 is in vitro, ex vivo or in vivo.

8. A method for inhibiting or preventing the binding of a cofilin to an F-actin, comprising:
(i) (a) providing a pharmaceutical, formulation or composition
comprising a compound ZINC04307500 having the structure:

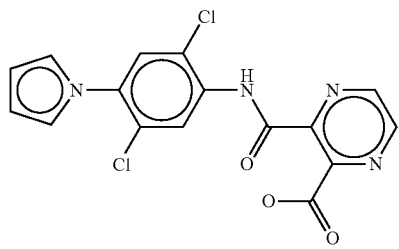

and
(b) contacting the pharmaceutical compound, formulation or composition of (a) with a SSH-2 or SlingShot-2 polypeptide in the cell in an amount sufficient to inhibit or slow the dephosphorylating of the cofilin, thereby inhibiting or preventing the binding of a cofilin to an F-actin; or
(ii) the method of (i), wherein the contacting of the compound or composition with the SSH-2 is in vitro, ex vivo or in vivo.

9. A method for stabilizing F-actin polymers, actin filaments, or actin-comprising microtubules, in a cell, comprising:
(i) (a) providing a pharmaceutical, formulation or composition
comprising a compound ZINC04307500 having the structure:

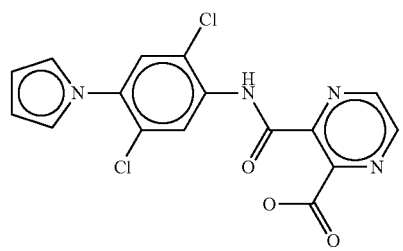

or any analog or derivative thereof stereoisomer or bioisostere thereof; and
(b) administering the pharmaceutical compound, formulation or composition of (a) to the cell or, inserting the pharmaceutical compound or composition into the cell, in an amount sufficient to stabilize the F-actin polymer, actin filament, or actin-comprising microtubule; or
(ii) the method of (i), wherein the administering of the pharmaceutical compound, formulation or composition to the cell is in vitro, ex vivo or in vivo.

10. A method for stabilizing F-actin polymers, actin filaments, or actin-comprising microtubules, in a cell, comprising:
(i) (a) providing a pharmaceutical, formulation or composition
comprising a compound ZINC04307500 having the structure:

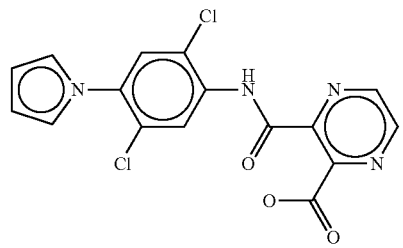

and
(b) administering the pharmaceutical compound, formulation or composition of (a) to the cell or, inserting the pharmaceutical compound or composition into the cell, in an amount sufficient to stabilize the F-actin polymer, actin filament, or actin-comprising microtubule; or
(ii) the method of (i), wherein the administering of the pharmaceutical compound, formulation or composition to the cell is in vitro, ex vivo or in vivo.

11. A method for decreasing cell motility, comprising:

(i) (a) providing a pharmaceutical, formulation or composition comprising a compound ZINC04307500 having the structure:

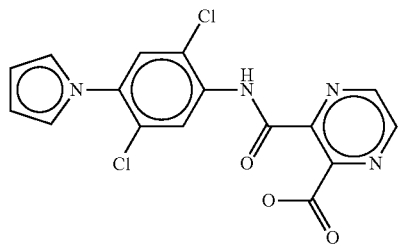

or any analog or derivative thereof or a stereoisomer or a bioisostere thereof; and (b) administering the pharmaceutical compound, formulation or composition of (a) to the cell or, inserting the pharmaceutical compound or composition into the cell, in an amount sufficient to decrease the cell's motility; or (ii) the method of (i), wherein the administering of the pharmaceutical compound, formulation or composition to the cell is in vitro, ex vivo or in vivo.

12. A method for decreasing cell motility, comprising:

(i) (a) providing a pharmaceutical, formulation or composition comprising a compound ZINC04307500 having the structure:

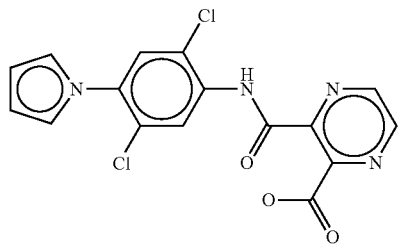

and (b) administering the pharmaceutical compound, formulation or composition of (a) to the cell or, inserting the pharmaceutical compound or composition into the cell in an amount sufficient to decrease the cell's motility; or (ii) the method of (i), wherein the administering of the pharmaceutical compound, formulation or composition to the cell is in vitro, ex vivo or in vivo.

13. A method for ameliorating a disease or condition responsive to inhibiting or decreasing cell motility and/or stabilizing F-actin polymers, actin filaments, or actin-comprising microtubules in a cell, comprising:

(i) (a) providing a pharmaceutical, formulation or composition comprising a compound ZINC04307500 having the structure:

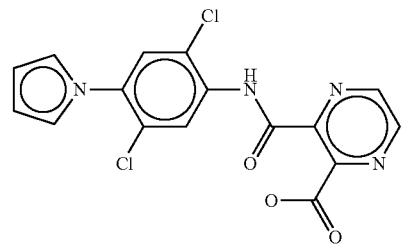

or any analog or derivative thereof or a stereoisomer or a bioisostere thereof; and (b) administering the pharmaceutical compound, formulation or composition of (a) to an individual in need thereof in an amount sufficient to inhibit or decrease cell motility and/or stabilize F-actin polymers, actin filaments, or actin-comprising microtubules; or (ii) the method of (i), wherein disease or condition ameliorated is cancer, a metastasis.

14. A method for ameliorating a disease or condition responsive to inhibiting or decreasing cell motility and/or stabilizing F-actin polymers, actin filaments, or actin-comprising microtubules in a cell, comprising:

(i) (a) providing a pharmaceutical, formulation or composition comprising a compound ZINC04307500 having the structure:

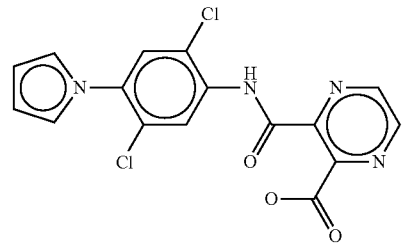

or any analog or derivative thereof or a stereoisomer or a bioisostere thereof; and (b) administering the pharmaceutical compound, formulation or composition of (a) to an individual in need thereof in an amount sufficient to inhibit or decrease cell motility and/or stabilize F-actin polymers, actin filaments, or actin-comprising microtubules; or (ii) the method of (i), wherein disease or condition ameliorated is Alzheimer's disease.

15. A method for decreasing or inhibiting cell growth, comprising:
(i) (a) providing a pharmaceutical, formulation or composition
comprising a compound ZINC04307500 having the structure:

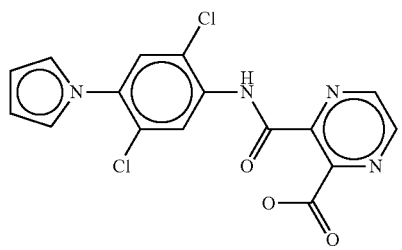

or any analog or derivative thereof or a stereoisomer or a bioisostere thereof; and
(b) administering the pharmaceutical compound, formulation or composition of (a) to the cell or; inserting the pharmaceutical compound or composition into the cell, in an amount sufficient to decrease or inhibit cell growth; or
(ii) the method of (i), wherein the administering of the pharmaceutical compound, formulation or composition to the cell is in vitro, ex viva or in vivo.

16. A method for decreasing or inhibiting cell growth, comprising:
(i) (a) providing a pharmaceutical, formulation or composition
comprising a compound ZINC04307500 having the structure:

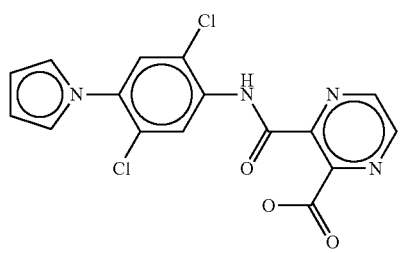

and
(b) administering the pharmaceutical compound, formulation or composition of (a) to the cell or, inserting the pharmaceutical compound or composition into the cell, in an amount sufficient to decrease or inhibit cell growth; or
(ii) the method of (i), wherein the administering of the pharmaceutical compound, formulation or composition to the cell is in vitro, ex vivo or in viva.

17. The pharmaceutical compound, formulation, or composition of claim 1, where the pharmaceutical compound, formulation, or composition comprises a 3-[(4,5-dimethoxy-3-oxo-1H-isobenzofuran-1-yl)amino]-4-methylbenzoic acid.

18. The pharmaceutical compound, formulation, or composition of claim 1, where the pharmaceutical compound, formulation, or composition comprises a 2-ethoxy-5-(4-phenylpiperidine-1-sulfonyl)benzoic acid.

19. The pharmaceutical compound, formulation, or composition of claim 1, where the pharmaceutical compound, formulation, or composition comprises a 3-[bis(2-methoxyethyl)sulfamoyl]benzoic acid.

20. The pharmaceutical compound, formulation, or composition of claim 2, where the pharmaceutical compound, formulation, or composition comprises a compound ZINC04307500 having the structure:

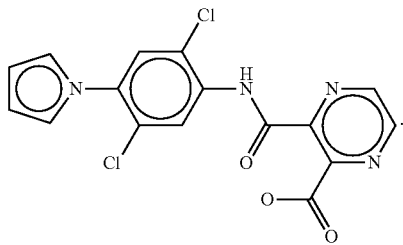

21. The pharmaceutical compound, formulation, or composition of claim 2, where the pharmaceutical compound, formulation, or composition comprises a compound having the structure:

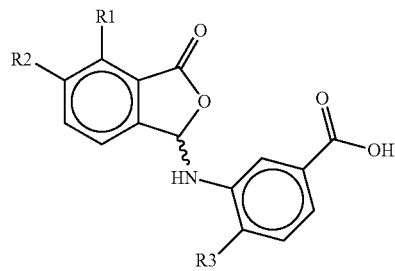

wherein R1 and R2 can be any alkoxy group, methoxy-group, ethoxy- group, butoxy- group, or a group having a longer alkyl or alkene group, or any combination thereof, and R3 can be any alkyl group, including a methyl, ethyl, propyl or butyl or longer alkyl or alkene group, or any combination thereof; or any analog or derivative thereof or a stereoisomer or a bioisostere thereof.

* * * * *